Aug. 4, 1953 H. L. GILLESPIE Plant Pat. 1,208
AVOCADO TREE
Filed July 30, 1951
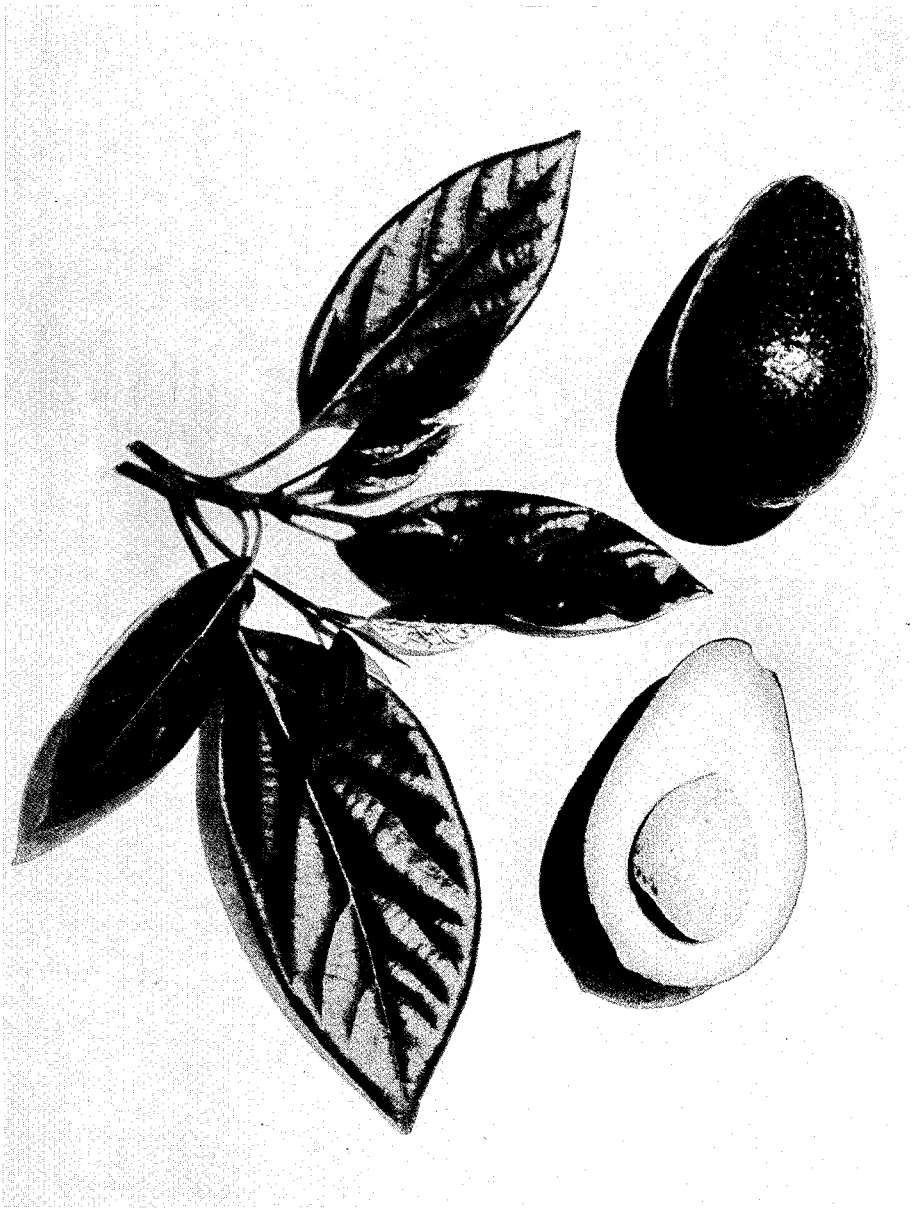
HERBERT L. GILLESPIE,
INVENTOR.
By C. A. Wilkinson
ATTORNEY.

Patented Aug. 4, 1953

Plant Pat. 1,208

UNITED STATES PATENT OFFICE 1,208

AVOCADO TREE

Herbert L. Gillespie, San Gabriel, Calif.

Application July 30, 1951, Serial No. 239,210

1 Claim. (Cl. 47—62)

This invention relates to a new and distinct variety of avocado tree having certain highly desirable characteristics.

Commercially acceptable avocado trees should not bear excessively large fruit, since for household use it is believed that fruit of between about 6 oz. and 10 oz. each is best adapted for marketing. Furthermore, the fruit should have a relatively high oil content, its flesh should be substantially free from fiber and be of a light color, free from the tendency to darken or discolor adjacent the seed or nut. The nut should not be large in order to minimize the proportion of edible flesh. At the present time popular demand desires pyri form fruit of a green coloration with a relatively thin skin. The fruit should have the ability to ship well and maintain quality during storage, shipment and handling.

From the standpoint of the grower, the trees should not have a very irregular or excessively spreading habit of growth nor should the trees have a very tall, slim habit of growth, since under the latter conditions picking of the fruit from the upper branches entails high labor costs. The tree therefore should be of a regular habit of growth and have foliage characteristics which adequately protect the bark and fruit from sunburn and windburn. The wood should not be brittle as in some varieties and preferably the tree should not exhibit the alternate bearing habit which is characteristics of many varieties. Moreover, the tree should be relatively resistant to light frost and its fruit should reach horticultural maturity over a protracted period of time so as not to flood the market with its fruit because of a brief bearing period.

It is believed that the tree of my new variety, which originated as a cultivated seeedling, answers all of the general requirements enumerated hereinabove. Some of its desirable characteristics may be due to the manner in which the seedling was germinated hydroponically and was originally propagated in Los Angeles County, California. After such germination and selection, the seedling was potted and permitted to grow to an appreciable size so that a dense, matted root ball was formed. Thereafter the young tree was permanently transplanted in the ground. The seed thus raised into the parent tree is believed to have been of a Guatemalan variety. Although the parent tree did not exhibit excessive vigour when it was transplanted into the field, its grafts and nursery stock exhibit acceptable vigour. The tree produces excellent budwood, with very little shedding even when small buds are used. Budding and grafting on different root stocks have been successfully carried out in Los Angeles County.

The terminal foliage, as well as the fruit itself, is illustrated in the appended color photograph.

The new variety of avocado to which this invention is directed is a tree characterized by a regular, opposite-branching habit of growth without the irregularity and widely spreading characteristics of the Fuerte (unpatented). The foliage of the tree is distinctive in that the young leaves are open and flat with a minor proportion slightly concave longitudinally; mature leaves are substantially flat both longitudinally and transversely, with some tendency to become slightly convex longitudinally. The leaves are virtually free from ruffling or undulation at the edges, some very minor ruffling being evidenced only in very old leaves. The leaf growth is not bunchy but instead fairly uniform along the foliated branches, thereby adequately protecting the branches and fruit.

All leaves are simple, elongated and bifacient, and emanate from nodes which are fairly well spaced. The branches, including the tips, extend in upward directions. Young leaves are reddish, exhibiting shades such as Medal Bronze, Auburn and Mars Brown. (Ridgway, Color Standards, Plates IV, II and XV, with distinct veining in Parrot Green, or Yellowish Oil Green (Plates VI and V). The lower side of the leaves is Fuscous, Dusky Brown or Hays Brown (Plates XLVI, XLV and XXXIX). Young leaves and flush wood have a pronounced anise odor when crushed.

Mature leaves are glossy and somewhat greener than Dark Cress, Hellebore or Cedar Green (Plates XXXI, XVII and VI) and sometimes are Varley's Green (Plate XVIII). The underside is dull and Vetiver Green or Bice Green in color (Plates XLVII and XVII).

Young stems are deep Chrysotile Green to light Cress Green in color (Plate XXXI) with numerous long and narrow ferruginous lenticels. Maximum defoliation, at the location of the parent tree at Pacific Palisades, county of Los Angeles, California, appears to take place during flowering from about March to June, but is not excessive. Substantially no terminal flowering takes place; flower bud nodes are generally whorled or alternate and mostly adventitious, with only occasional axillary flower buds. Bud nodes occur with short nodal spacing, much closer together than the leaf nodes. The tree appears to have a protracted flowering period from about the middle of March to early June in its present coastal location. At temperatures above 70° F. the stamens discharge pollen in less than two hours after initial opening, at which time the stigma is soft and receptive. Usually three of the stamens remain erect in a close group about the pistil during this initial opening.

One of the important characteristics of the tree is its ability to hold or retain fruit on the tree for a protracted period of time. Full grown fruit can be found on the tree even during flowering, and this, coupled with a protracted flowering period, permits fruit to be picked from the tree throughout the year.

The fruit is pyriform, green in color (Cerro Green to Varley's Green, Plates V and XVIII) with the stem button slightly offset to the side. The stems are relatively short, varying from about 2½ in. to 3 in. in length and are firmly attached but without a deep button cavity. The seed is of medium size, slightly pointed, and has two lobes; fruit vary in size from about 6 oz. to 10 oz. and the seeds range from about 1 oz. to 1¾ oz. The seed is provided with a brown, closely adhering covering and is easily separated from the flesh in the mature fruit; at no time has a loose seed been found in a mature fruit. Stomata are not evenly distributed over the area of the fruit, greater concentrations occurring at the apical end. The stomata occur in slightly elevated areas of the skin surface and are lighter green in color, often with a ferruginous center.

The flesh of the fruit is firm, substantially free from fibers and of excellent flavor. The main body of flesh is Baryta Yellow, merging into light green adjacent the skin, the color varying somewhat with ripeness of the fruit. Oil content of the flesh has been determined at various times with the following results:

| Fruit Picked | Flavor | Oil Content, Percent |
|---|---|---|
| June | Good | 24.2 |
| July | Excellent | 28.2 |
| August | Excellent plus | 21.8 |
| September | Good plus | 31.0 |
| October | Excellent | 24.0 |
| November | Good plus | 29.0 |
| December—*a* | Excellent | 28.5 |
| December—*b* | Good minus | 13.1 |
| January—*a* | Excellent | 28.5 |
| January—*b* | Good | 14.0 |
| February—*a* | Good plus | 27.4 |
| February—*b* | do | 17.5 |
| March | Good | 19.8 |
| April | Good plus | 19.5 |
| May | do | 21.0 |

It is to be noted that all of the fruit tested was from a single tree. Attention is called to the fruit picked during December, January and February; the fruit picked during these three months indicates that the tree held fruit fourteen months past horticultural maturity. The flavor and oil results were by accredited and impartial experts.

The distinguishing characteristics of the tree of this invention appear to be the flat character of its leaves (with some tendency to longitudinal convexity), its prolonged flowering period, which insures the setting of fruit and reduces possibility of low setting due to spring winds, and the ability of the tree to carry fruit at various stages of maturity throughout the year, thereby permitting picking during the entire calendar year. It is to be understood that departures from the specific description given herein will occur due to climatic conditions, distance from the ocean, humidity conditions, soil variations etc. As at present advised, it is believed that the tree is eminently suited for commercial planting in the coastal and intermediate areas.

I claim:

A variety of avocado tree substantially as disclosed, characterized by substantially flat mature foilage, a prolonged flowering period and the ability to bear mature, green, pyriform fruit during the entire calendar year.

HERBERT L. GILLESPIE.

No references cited.